US010234451B2

(12) United States Patent
Ramji et al.

(10) Patent No.: US 10,234,451 B2
(45) Date of Patent: Mar. 19, 2019

(54) ASSAY DEVICE

(71) Applicant: National University of Singapore, Singapore (SG)

(72) Inventors: Ramesh Ramji, Singapore (SG); Fook Chiong Cheong, Singapore (SG); Chwee Teck Lim, Singapore (SG)

(73) Assignee: National University of Singapore, Singapore (SG)

( * ) Notice: Subject to any disclaimer, the term of this patent is extended or adjusted under 35 U.S.C. 154(b) by 690 days.

(21) Appl. No.: 14/846,371

(22) Filed: Sep. 4, 2015

(65) Prior Publication Data

US 2016/0069874 A1 Mar. 10, 2016

(30) Foreign Application Priority Data

Sep. 8, 2014 (GB) .................................. 1415804.2

(51) Int. Cl.
| C12M 3/06 | (2006.01) |
| G01N 33/543 | (2006.01) |
| G01N 33/569 | (2006.01) |
| C12M 1/12 | (2006.01) |
| C12M 1/00 | (2006.01) |
| C12M 1/34 | (2006.01) |

(52) U.S. Cl.
CPC ....... *G01N 33/54366* (2013.01); *C12M 23/16* (2013.01); *C12M 25/02* (2013.01); *C12M 29/10* (2013.01); *C12M 41/38* (2013.01); *G01N 33/56966* (2013.01)

(58) Field of Classification Search
None
See application file for complete search history.

(56) References Cited

U.S. PATENT DOCUMENTS

| 2002/0106786 A1* | 8/2002 | Carvalho .............. B01F 5/0647 435/287.3 |
| 2007/0134807 A1 | 6/2007 | Bao et al. |
| 2009/0023608 A1* | 1/2009 | Hung ................ B01L 3/502707 506/32 |
| 2010/0227312 A1 | 9/2010 | Pant et al. |
| 2011/0223627 A1 | 9/2011 | Neeves et al. |
| 2014/0127508 A1 | 5/2014 | Saif et al. |
| 2014/0199745 A1 | 7/2014 | Voldman et al. |

FOREIGN PATENT DOCUMENTS

| EP | 2535721 A1 | 12/2012 |
| WO | WO2007/047644 A2 | 4/2007 |
| WO | WO2008/079320 A1 | 7/2008 |
| WO | WO2009/100028 A1 | 8/2009 |
| WO | WO2009/102453 A2 | 8/2009 |
| WO | WO2010/108095 A2 | 9/2010 |
| WO | WO2012/050981 A1 | 4/2012 |

* cited by examiner

*Primary Examiner* — Rebecca L Martinez
(74) *Attorney, Agent, or Firm* — Klarquist Sparkman, LLP

(57) ABSTRACT

The disclosure relates to a method and device for detecting and quantifying biological molecules such as cell surface or intracellular ligands/receptors in a dynamic system with high sensitivity and specificity; the method of using such platform optionally in combination with an optical detection system and kits comprising the optical platform.

34 Claims, 10 Drawing Sheets
(9 of 10 Drawing Sheet(s) Filed in Color)

FIG. 1A Microfluidic Device
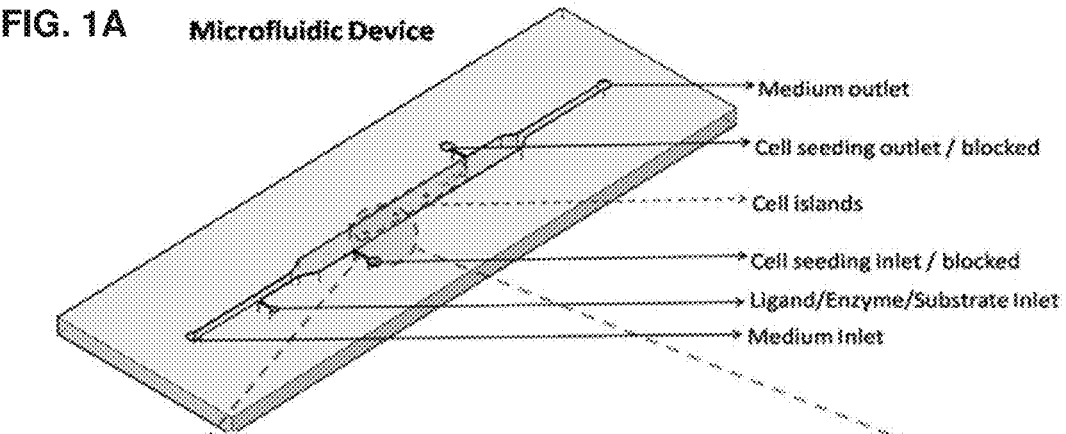
FIG. 1B Side View
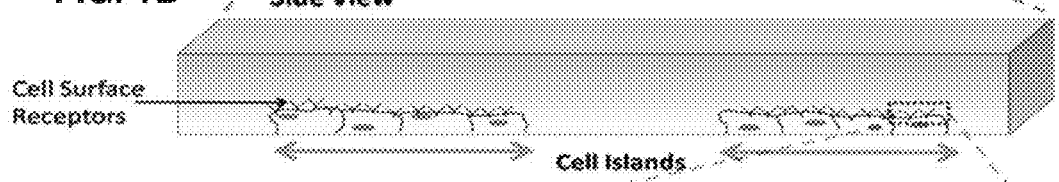
FIG. 1C Cell Surface
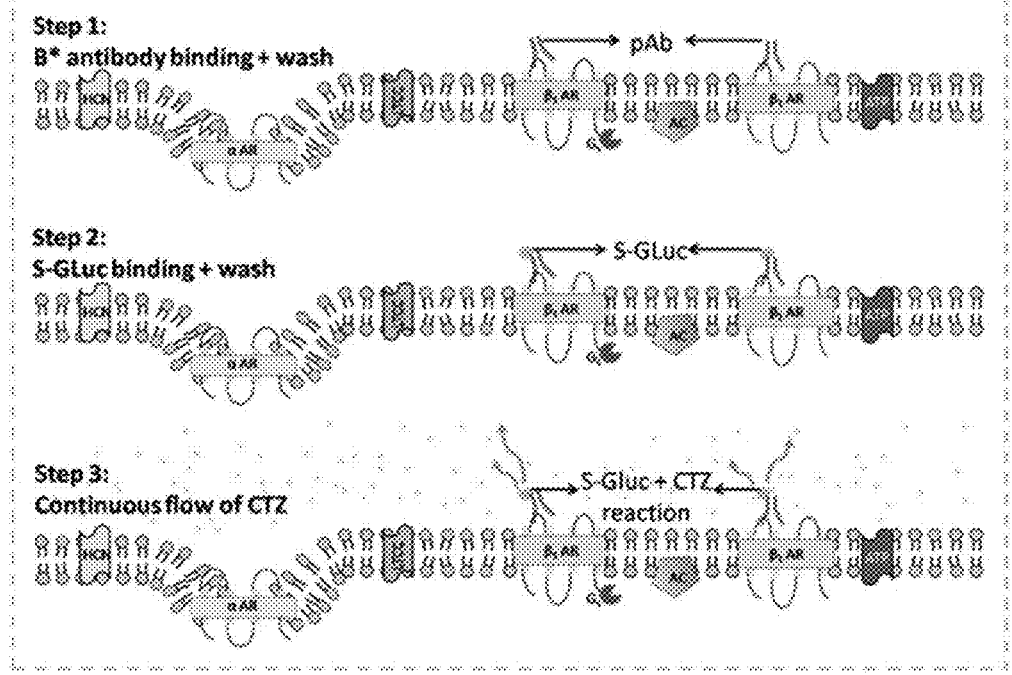

FIG. 2A FIBRONECTIN PATTERNING
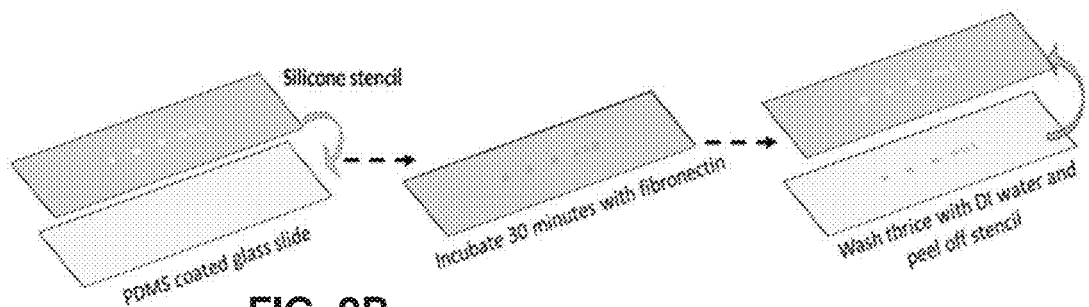
FIG. 2B ENZYME CALIBRATION
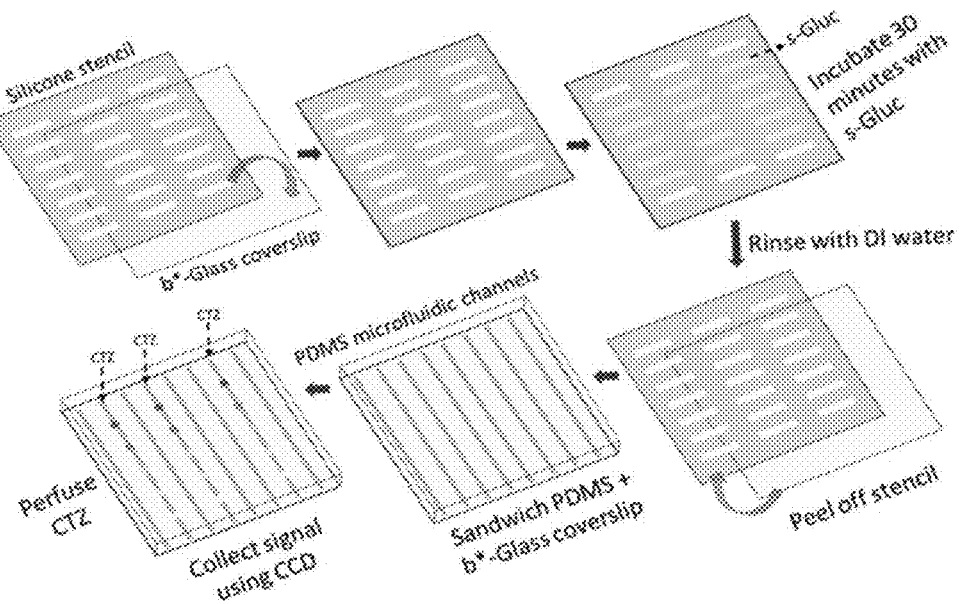

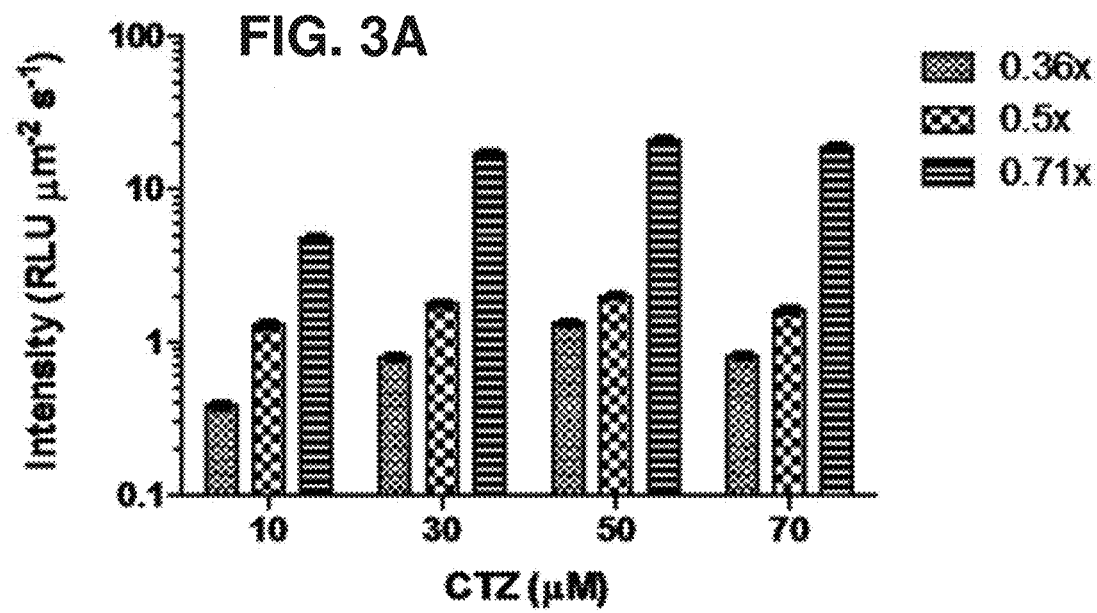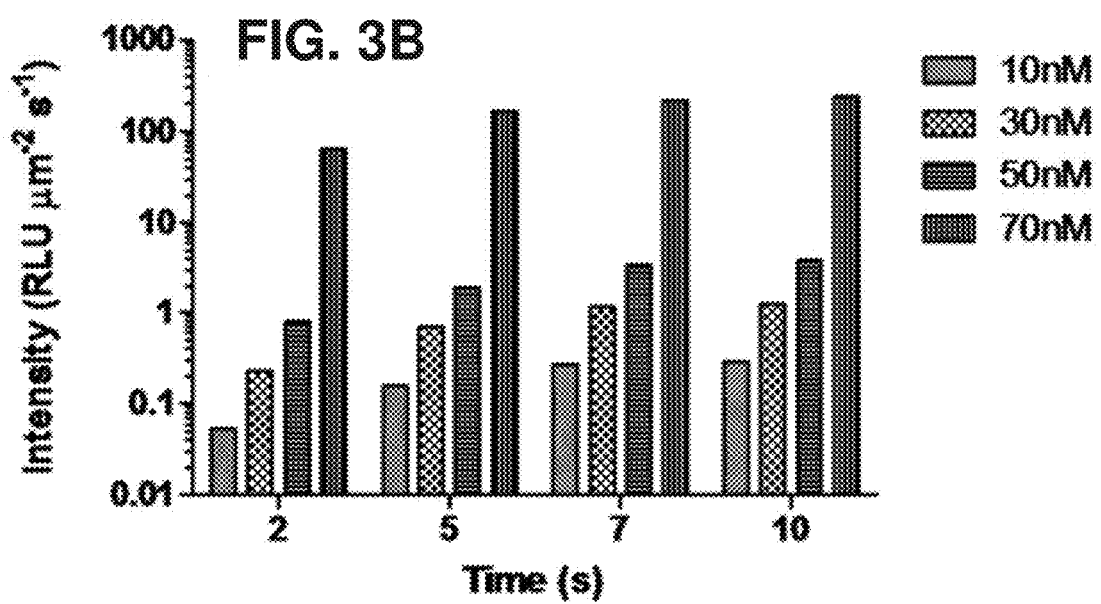

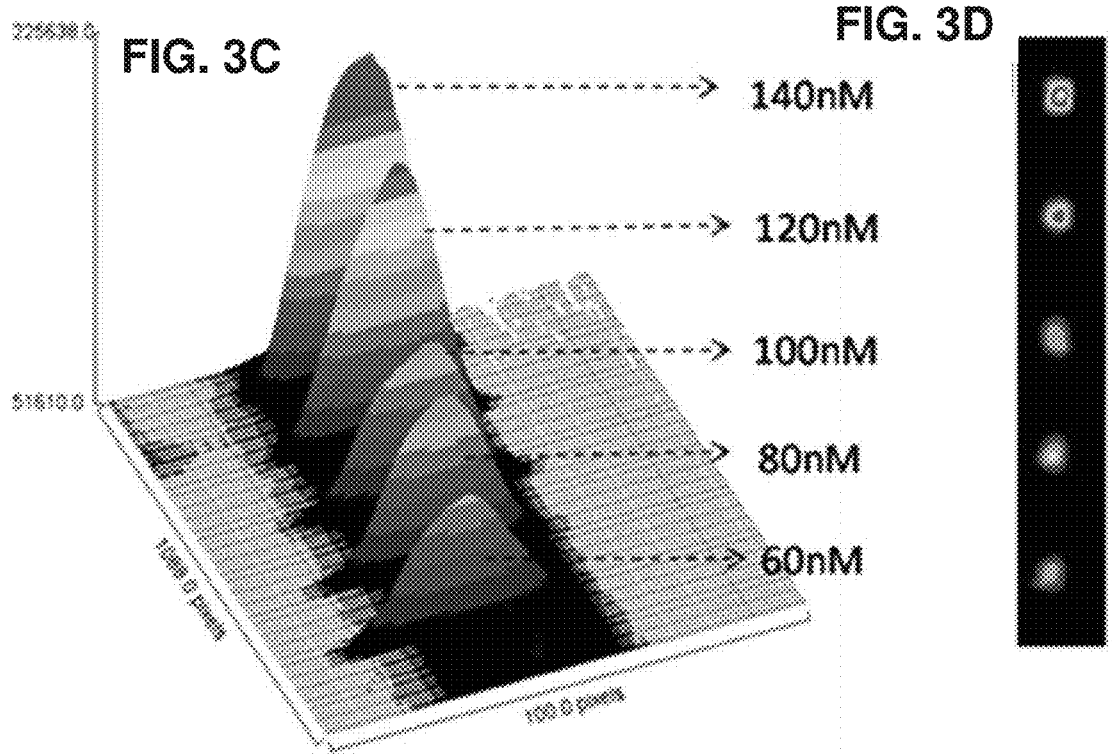
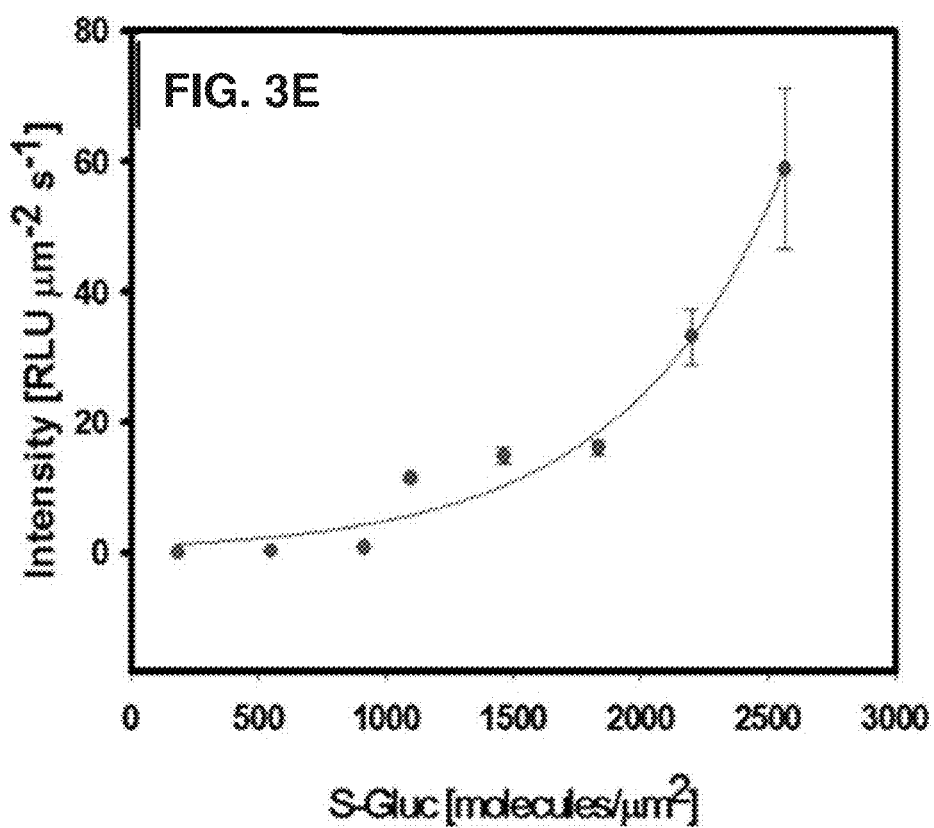

FIG. 4A
Bioluminescence signal
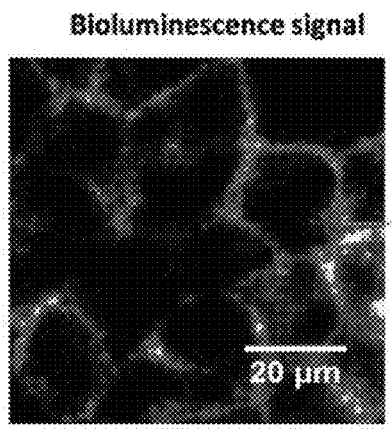
FIG. 4B
Fluorescence signal
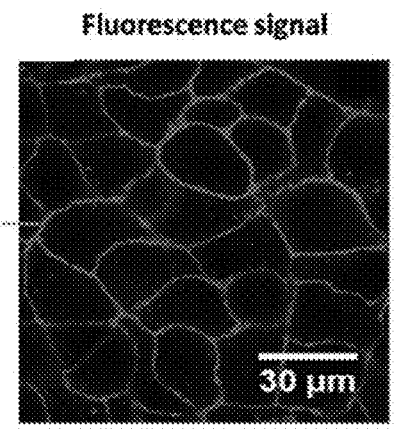
Cell surface
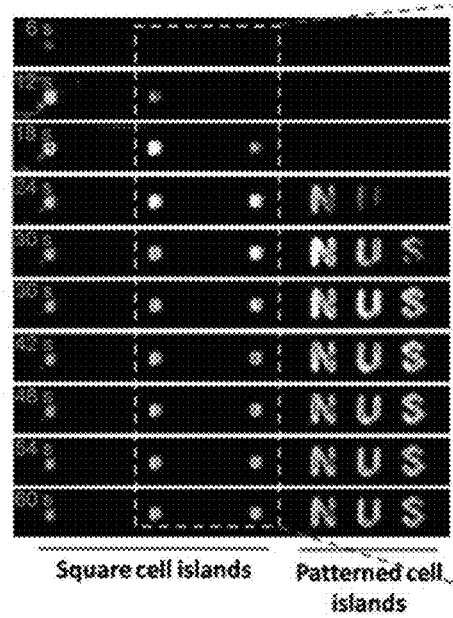
Microchannel flow signal
Square cell islands | Patterned cell islands
FIG. 4C
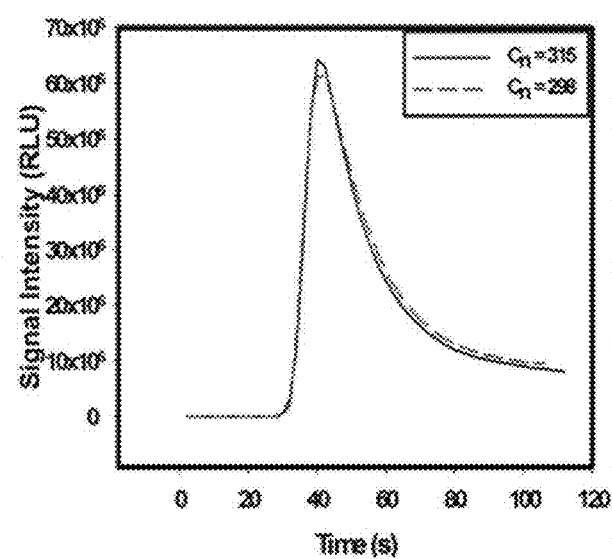
Cell Islands Intensity Plot
FIG. 4D

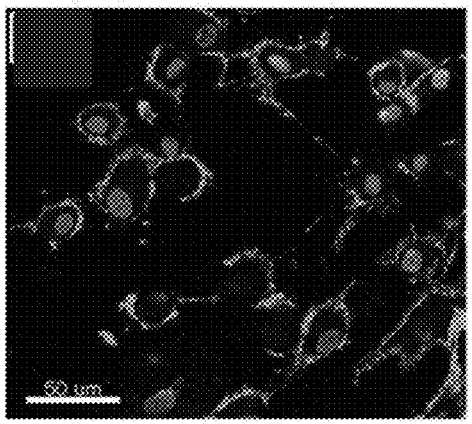
FIG. 5A
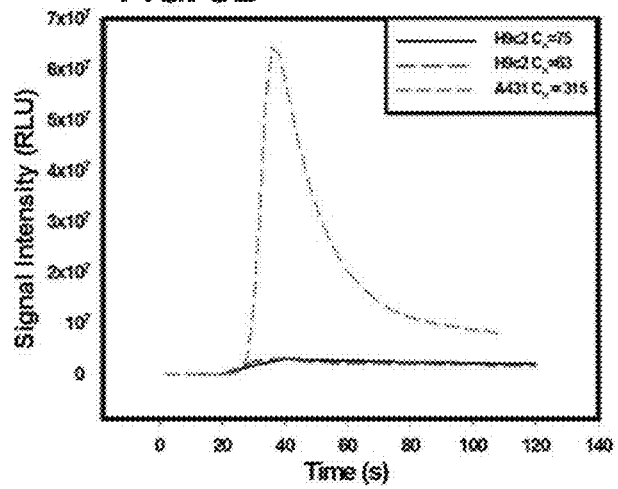
FIG. 5B
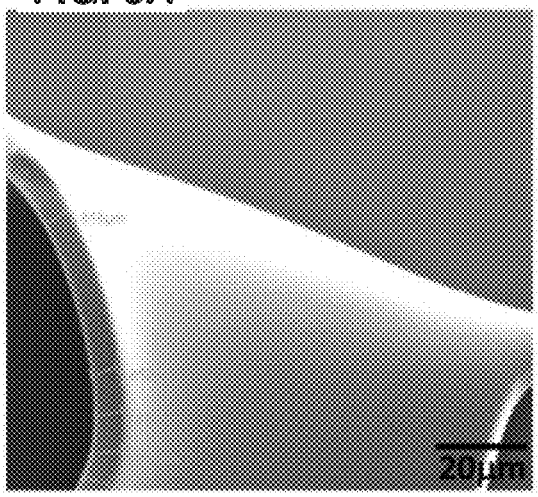
FIG. 6A
PDMS coating ≈ 6μm
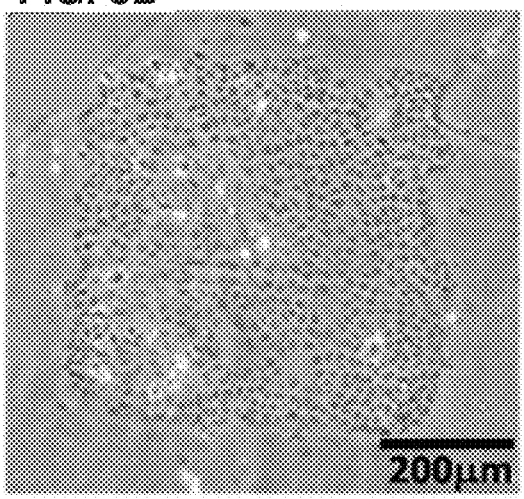
FIG. 6B
Square cell island
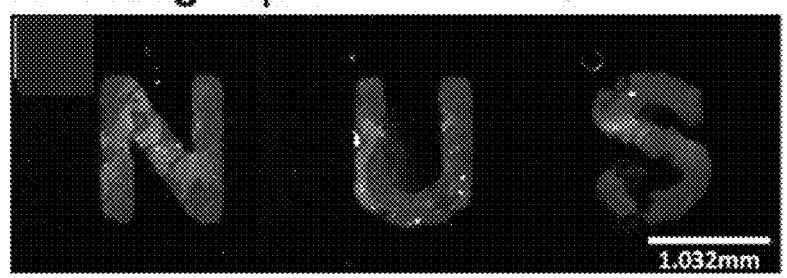
FIG. 6C  Fluorescent fibronectin pattern on PDMS coated glass coverslip FIG. 7A
A431 cell
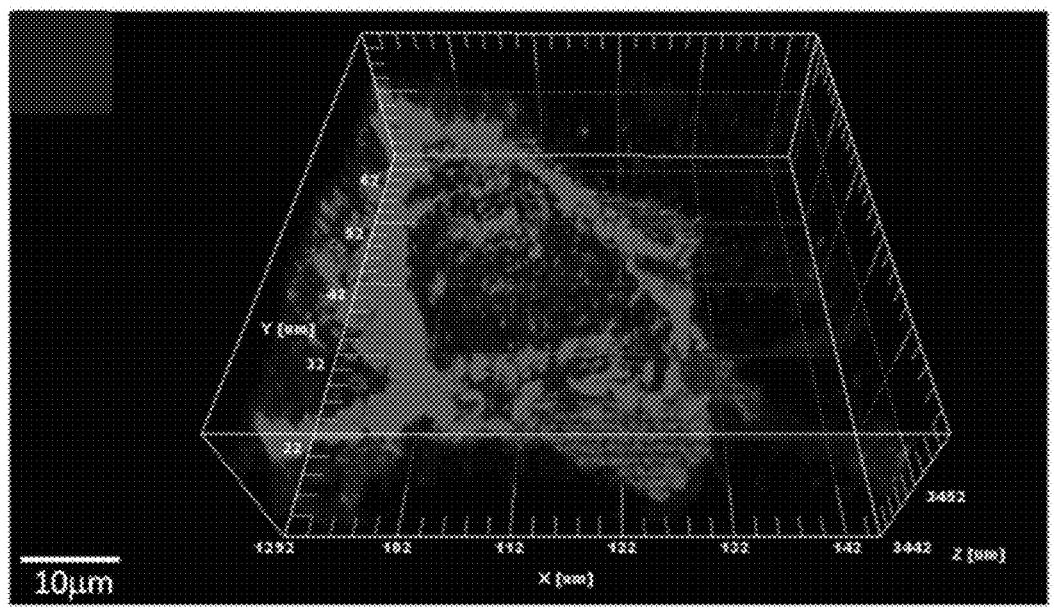
H9c2 cells
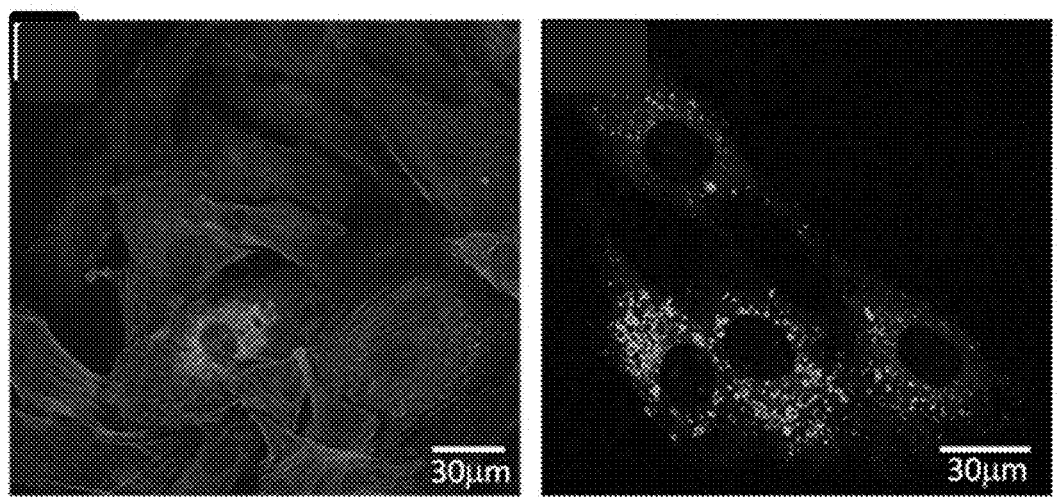
FIG. 7B
FIG. 7C Step 1: Cell Seeding Media Inlet
Media Outlet Step 2: Cell Feeding and Growth Cell seeding Inlet
Cell seeding Outlet

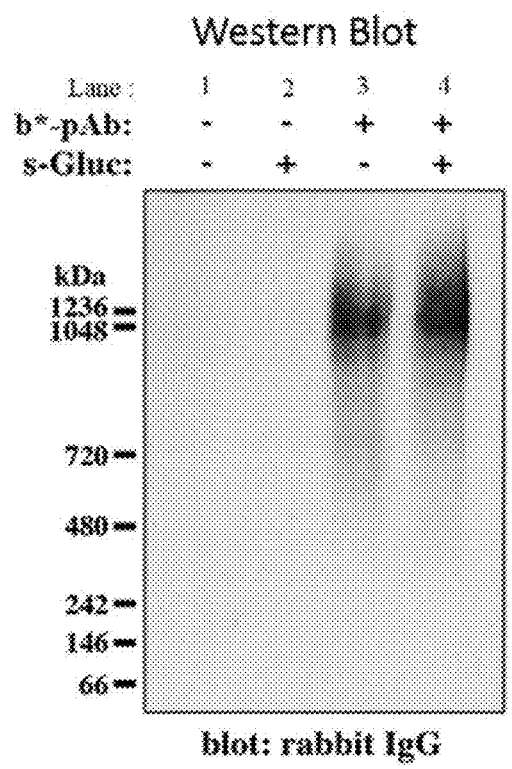
FIG. 9A
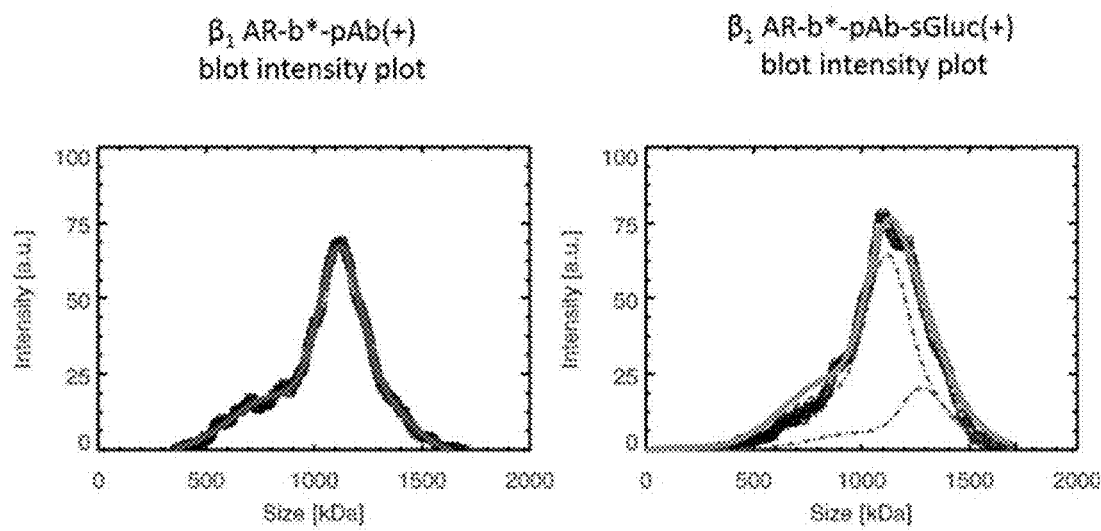
FIG. 9B          FIG. 9C

ASSAY DEVICE

CROSS-REFERENCE TO RELATED APPLICATION

This application claims profit to Great Britain Application No. 1415804.2, filed Sep. 8, 2014, herein incorporated by reference.

FIELD OF THE INVENTION

The disclosure relates to a method for detecting and quantifying biological molecules such as cell surface and/or intracellular ligands/receptors in a dynamic system with high sensitivity and specificity; the method of using such platform optionally in combination with a lens free optical detection system.

BACKGROUND OF THE INVENTION

The development of microfluidic devices, or so called lab-on-a-chip, enabled the miniaturization of large-scale laboratory systems to the size of a chip and has several advantages over conventional methods such as portability, reduction in the amount of reagents and sample, easy implementation of high throughput methods and its small size. Microfluidic devices have various applications in biotechnology and pharmaceutical industry from oxygenation devices, sequencing chips, analytic devices, micro-fuel cells to "plant on a chip", which are microfluidic chips developed for stimulating for example plant roots with various chemicals. WO2010/018499 discloses microfluidic devices for cellular susceptibility testing via a concentration gradient, and others such as CN201628717 disclose a microfluidic chip for detecting pathogenic bacteria by bioluminescence based on the recombinant firefly luciferase detection system.

Bioluminescence is frequently used in reporter assays, monitoring tumour growth and in vivo imaging (10, 11) and is based on an enzymatic reaction which results in the detectable emission of light. The reaction is based on the conversion of the substrate luciferin to oxyluceferin by the luciferase enzyme which results in emission of light. This oxidative reaction is usually, ATP dependent as in firefly luciferase. Unlike fluorescence, bioluminescence does not require an external light source to excite the chemical reaction thus avoiding photo-bleaching effects. In addition, the virtually zero background allows one to detect bioluminescent signals with high sensitivity. This property of bioluminescence makes it a robust method for high throughput cell screening assays (12-14).

Other luciferase enzymes such as the Gaussia luciferase (GLuc) (9), derived from the marine copepods, brighter when compared to Firefly or Renilla Luciferases (15) and, most importantly, the light emitting reaction is ATP independent. Thus artefacts commonly caused by cellular ATP during signal generation have no effect on the signal generated.

Cell surface receptors play an important role in signal communication and response. The development of a diseased state can also be due to changes in receptor density through up-regulation or down-regulation and a disturbed balance in the (in) activation of the receptors (1). For instance, the change in dopamine D2 receptors in Parkinson's disease and myocardial β1 adrenoceptor down regulation in heart failure are good examples to portray the effect of receptor number on diseases (2, 3).

Thus, there is a need to quantify the number of receptors expressed on both healthy and diseased cells.

There are several approaches to quantify receptor expression in cells. Methods such as the saturation and competitive binding techniques are often used to determine receptor numbers in live or fixed cells (4). The use of radio-labels in the case of saturation and competition binding methods is problematic. Recent developments in near-field scanning optical microscopy (NSOM) techniques using fluorescent probes have also enabled a deterministic method of distribution and quantification of cell surface receptors (5, 6). A localized evanescent wave produced at the tip of the NSOM probe helps to excite the receptor bound fluorescent-ligand to get an image of a target receptor at the nanometer scale resolution. Although the near field imaging technique is a very good method for quantifying cell surface receptors, it works best on fixed cells where the probe to sample distance can be controlled more accurately using a force-feedback loop. In addition, photo-bleaching of the fluorophores can also commonly occur on dry samples due to direct contact with air (7, 8).

This disclosure relates to an assay device, such as a microfluidic device, based bioluminescence and its use in a method to quantify cell surface ligands/receptors. In addition the method can also quantify intracellular receptors by permeabilizing the cell membrane. The device provides an improved, highly sensitive and specific dynamic system for the growth of cells and detection of cell surface molecules on living cells. In addition, without the need for an external illumination, the size of the equipment can be reduced, and as signals detected are directly related to the concentration of the molecule being studied. The approach allows real time signal detection with fast response times.

STATEMENTS OF INVENTION

According to an aspect of the invention there is provided an assay device for the dynamic analysis of cell surface and/or intracellular ligand/receptor expression by live cells comprising a cell culture support having one or more cell culture channels wherein said channel[s] are adapted by the provision of a cell support matrix comprising one or more cell adhesion/cell growth factors over all or part of the cell culture channel to provide a cell culture surface wherein said channel[s] are provide with at least first and second openings positioned at or near the ends of said channel[s] to provide fluid passage into said channel[s].

In an embodiment of the invention said cell culture support comprises a plurality of cell culture channels.

In a further embodiment of the invention said first and second openings are adapted to receive cell growth medium.

In a further embodiment of the invention said channel[s] are provided with a further opening, optionally closable, positioned separately from the first or second openings, and in fluid contact with said cell culture channel[s].

In an embodiment of the invention said further opening is adapted to receive a sample comprising one or more cell types.

In a further embodiment of the invention said channel[s] are provided with a yet further opening, optionally closable, positioned separately from said first, second and third openings and in fluid contact with said cell culture channel[s].

In an embodiment of the invention said fourth opening is adapted to receive a sample comprising a binding agent that specifically binds a cell surface ligand/receptor.

In a further embodiment of the invention said first, second, third or fourth opening is adapted to receive, either continuously or intermittently, a test agent wherein the test agent modulates, either directly or indirectly, cell function of a cell contained in said cell culture channel.

In an embodiment of the invention said cell culture support comprises silicone.

In an embodiment of the invention the silicone is polydimethylsiloxane.

In an alternative embodiment of the invention said cell culture support comprises plastic or example polystyrene or nylon.

In a embodiment of the invention said cell support matrix comprises one or more cell adhesion proteins selected from the group: fibronectin, laminins, collagens and adherins.

The provision of cell culture surface will facilitate the growth and differentiation of cells applied to the cell culture channel. Cell culture agents are typically proteins or glycoproteins. Proteins involved in maintaining the proliferation and/or differentiation of cells are well known. For example, typical protein factors include extracellular matrix proteins such as fibronectin, laminins, collagens, cadherins and fibroblast growth factors but also included in the scope of the invention are monokines and cytokines which are, depending on cell-type, required to maintain cell proliferation and/or differentiation. In addition carbohydrate agents such as lectins are well known to be involved in promoting cell differentiation and forming cell to cell contacts between similar and dissimilar cell types. Poly-amino acids have properties that mimic proteins and in particular proteins to which cells can attach and grow. Poly-amino acids can be homopolymers or heteropolymers. Examples of poly amino acids useful in cell culture include poly L ornithine and poly L lysine. Proteinaceous coatings are well known in the art. For example see Culture of Animal Cells, Ian Freshney, Wiley-Liss 1994.

In an embodiment of the invention said the plurality of cell culture channels comprises the same cell support matrix.

In an alternative embodiment of the invention said the plurality of cell culture channels comprises a different cell support matrix.

In an embodiment of the invention said device comprises one or more cell types.

In an embodiment of the invention said cell type is a mammalian cell.

Said mammalian is selected from the group consisting of: non-human primate, mouse, rat, hamster or rabbit.

In an embodiment of the invention said mammalian cell is human.

In an embodiment of the invention said mammalian cell is selected from the group consisting of: an epidermal keratinocyte, a fibroblast (e.g. dermal, corneal, intestinal mucosa, oral mucosa, bladder, urethral, prostate, liver) an epithelial cell (e.g. corneal, dermal, corneal; intestinal mucosa, oral mucosa, bladder, urethral, prostate, liver), a neuronal glial cell or neural cell, a hepatocyte or hepatocyte stellate cell, a mesenchymal cell, a muscle cell (cardiomyocyte or myotube cell), a kidney cell, a blood cell (e.g. CD4+ lymphocyte, CD8+ lymphocyte) a pancreatic β cell; or an endothelial cell).

In an embodiment of the invention said mammalian cell is a cardiomyocyte.

In an alternative embodiment of the invention said mammalian cell is a cancer or tumour cell.

In an embodiment of the invention said cell is a cancer cell derived from cancerous tissue.

As used herein, the term "cancer" or "tumour" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In an alternative embodiment of the invention said cell is a stem cell.

In an embodiment of the invention said embryonic stem cell/embryonic germ cell is a pluripotent cell and not a totipotent cell.

In an embodiment of the invention said stem cell is selected from the group consisting of: haemopoietic stem cell; neural stem cell; bone stem cell; muscle stem cell; mesenchymal stem cell; epithelial stem cell (derived from organs such as the skin, gastrointestinal mucosa, kidney, bladder, mammary glands, uterus, prostate and endocrine glands such as the pituitary); endodermal stem cell (derived from organs such as the liver, pancreas, lung and blood vessels); embryonic stem cell; embryonic germ cell; embryonal carcinoma stem cell.

In a further embodiment of then invention said stem cell is a cancer stem cell.

In an embodiment of the invention said device is a microfluidic device.

According to a further aspect of the invention there is provided a cell culture apparatus comprising: an assay device according to the invention in fluid contact with a source of cell growth medium wherein the cell growth medium flows through said device to provide cell growth nutrients to cells contained within said assay device.

According to a further aspect of the invention there is provided a device according to the invention for use in assaying expression of cell surface ligands and/or receptors.

According to an aspect of the invention there is provided a method to assay the expression of one or more ligands/receptors expressed by a cell comprising the steps:
  i) providing an assay device according to the invention;
  ii) adding to said device via at least one of the openings at least one binding agent that binds one or more ligands/receptors expressed by a cell contained within said cell culture channel wherein said binding agent is detected, either directly or indirectly by a detectable label; and
  iii) detecting the binding of the binding agent to said one or more ligands/receptors as a measure of the presence of said ligand/receptor.

In an embodiment of the method of the invention said binding agent is a biomolecule.

In an embodiment of the method of the invention said binding agent is an antibody or antibody binding fragment.

In an alternative embodiment of the method of the invention said binding agent is a ligand that specifically binds said receptor.

In a further embodiment of the method of the invention said binding agent is a receptor that specifically binds said ligand.

In an embodiment of the method of the invention said detectable label is a bioluminescent label.

In an embodiment of the method of the invention said binding agent is a fusion protein comprising a polypeptide binding agent fused in frame to a bioluminescent polypeptide.

Said bioluminescent polypeptide is a luciferase or a modified luciferase.

In an embodiment of the method of the invention said device comprises a plurality of cell culture channels comprising one or more cell types arranged in an array and adapted to be read by an array reader.

In an embodiment of the method of the invention said method is a diagnostic or prognostic method and said cell sample is an isolated biological sample from a subject.

In an embodiment of the method of the invention said subject is human.

According to a further aspect of the invention there is provided a screening method for the identification of agents that modulate the activity of a cell comprising the steps:
  i) providing an assay device according to the invention;
  ii) adding to said device via at least one of the openings at least one test agent to be screened for biological activity; and
  iii) measuring the activity of the test agent compared to a device or channel that has not been exposed to said test agent.

The screening of large numbers of agents requires preparing arrays of cells for the handling of cells and the administration of agents. Assay devices are typically used for compatibility with automated loading and robotic handling systems. Typically, high throughput screens use homogeneous mixtures of agents with an indicator compound which is either converted or modified resulting in the production of a signal. The signal is measured by suitable means followed by integration of the signals from each channel containing the cells, agent and indicator compound.

In an embodiment of the method of the invention said assay includes the steps of:
  i) collating the activity data above;
  ii) converting the collated data into a data analysable form; and optionally
  iii) providing an output for the analysed data.

The term "test agent" includes any small organic molecule/biomolecule, antibody, ligand, peptide, nucleic acid or peptide aptamer, double stranded or small inhibitory RNA. These can be an agonist or an antagonist. Small molecule antagonists include chemotherapeutic agents useful in the treatment of diseases such as cancer.

Some Specific Embodiments

Receptors and their ligands include differentiation, growth factors, polypeptide hormones, chemokines and cytokines, pro-inflammatory agents and pro-angiogenic agents.

Chemokine receptors are bound by chemokine polypeptides which refer to a group of structurally related low-molecular weight factors secreted by cells having mitogenic, chemotactic or inflammatory activities that activate receptors expressed by a range of cell-types. They are primarily cationic proteins of 70 to 100 amino acid residues that share four conserved cysteine residues. These proteins can be sorted into two groups based on the spacing of the two amino-terminal cysteines.

In the first group, the two cysteines are separated by a single residue (C-x-C), while in the second group they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and II (AMCF-I and -II), pre-B cell growth stimulating factor (PBSF), and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1-α), macrophage inflammatory protein 1β (MIP-1-β), macrophage inflammatory protein 1-γ (MIP-1-γ), macrophage inflammatory protein 3α (MIP-3-α, macrophage inflammatory protein 3β (MIP-3-β), chemokine (ELC), macrophage inflammatory protein-4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3.

A number of growth factors have been identified which promote/activate endothelial cells to undergo angiogenesis by receptor activation. These include vascular endothelial growth factor (VEGF A); VEGF B, VEGF C, and VEGF D; transforming growth factor (TGFb); acidic and basic fibroblast growth factor (aFGF and bFGF); and platelet derived growth factor (PDGF). VEGF is an endothelial cell-specific growth factor which has a very specific site of action, namely the promotion of endothelial cell proliferation, migration and differentiation. VEGF is a complex comprising two identical 23 kD polypeptides. VEGF can exist as four distinct polypeptides of different molecular weight, each being derived from an alternatively spliced mRNA. bFGF is a growth factor that functions to stimulate the proliferation of fibroblasts and endothelial cells. bFGF is a single polypeptide chain with a molecular weight of 16.5 Kd. Several molecular forms of bFGF have been discovered which differ in the length at their amino terminal region. However the biological function of the various molecular forms appears to be the same. bFGF is produced by the pituitary gland. Their receptors include VEGFR1, VEGFR2, VEGFR3, FGFR1, FGFR2, FGFR3 AND FGFR4, Further examples of growth factors include Insulin-like growth factor [IGF1] and growth hormone. IGF1 and its cognate receptor IGF1R in combination with human growth hormone are essential for normal growth and development. Additionally IGF1R has also been implicated in malignant transformation. The IGF1, IGF2 and insulin receptors are closely related and IGF1R can also be activated by IGF2. IGF1R consists of an alpha chain of approximately 740 residues disulphide linked to a transmembrane beta chain (90 kDa) which includes the cytoplasmic tyrosine kinase domain. Two alpha chains are disulphide linked so that the receptor forms an alpha2:beta2 tetramer on the membrane.

The alpha chain consists of several domains: two L domains, L1 (residues 1-150) and L2 (residues 300-460) are largely responsible for binding the hormone; the L domains are separated by a Cys-rich domain (151-299), and followed by fibronectin Type III domains (460-700) (Baserga R, Hongo A, Rubini M, Prisco M &Valentis B (1997) "The IGF-1 receptor in in cell growth, transformation and apoptosis" Biochim Biophys Acta 1332: F105-F126); Hubbard S B & Till, J H (2000) "Protein tyrosine kinase structure and function." Annu. Rev. Biochem. 59:373-398).

Cytokines are involved in a number of diverse cellular functions and activate cell surface receptors. These include modulation of the immune system, regulation of energy metabolism and control of growth and development. Cytokines mediate their effects via receptors expressed at the cell surface on target cells. Cytokine receptors can be divided into three separate sub groups. Type 1 (growth hormone (GH) family) receptors are characterised by four conserved cysteine residues in the amino terminal part of their extracellular domain and the presence of a conserved Trp-Ser-Xaa-Trp-Ser motif in the C-terminal part. The repeated Cys motif is also present in Type 2 (interferon family) and Type III (tumour necrosis factor family). Examples of cytokines include growth hormone, leptin, erythropoietin, prolactin, interleukins (IL) IL-2, IL-3, IL-4, IL-5, IL-6, IL-7, IL-9, IL-10, IL-11, the p35 subunit of IL-12, IL-13, IL-15, granulocyte colony stimulating factor (G-CSF), granulocyte macrophage colony stimulating factor (GM-CSF), ciliary neurotrophic factor (CNTF), cardiotrophin (CT-1), leukocyte inhibitory factor (LIF), interferon type I, II or III.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A & 1B illustrate a schematic representation of cell islands on fibronectin patterned area on a microfluidic chip. The fluidic inlets and outlets for perfusion of cell culture medium as well as reagents are indicated. FIG. 1C is a schematic representation of bioluminescence quantification of cell surface receptors. Light emission from s-Gluc (luciferase) conjugated antibodies bound to surface receptors occurs upon the addition of CTZ (luciferin).

FIG. 2A illustrates a method of patterning fibronectin onto PDMS-glass coverslip. A silicone stencil is used to pattern fibronectin onto a PDMS coated glass coverslip by adding and incubating fibronectin over it. Excess or unbound fibronectin is washed out by rinsing the glass coverslip thrice with DI water after which the stencil is removed. FIG. 2B illustrates a method of producing immobilized enzyme patterns to generate a calibration curve. Silicone stencil is first placed on the biotinylated glass coverslip and allowed to adhere firmly. Different dilutions of s-Gluc solutions are added carefully into the micro-wells. The stencil is removed after the incubation period. PDMS-microchannels sandwiched on top of the glass coverslip. This is followed by the injection of CTZ to produce light.

FIG. 3A illustrates the effect of substrate concentration [CTZ] on the total amount of light produced by the bioluminescence reaction. Error bars represent the standard deviation from the average light intensity produced (RLU μm-2s-1) calculated from area under the curve for 10, 20 and 30 second integrated times respectively. Varying apparent concentration of S-Gluc solutions 0.36, 0.5 and 0.71× was used in each well to form different immobilized Gluc densities respectively. FIG. 3B illustrates the effect of exposure time in the total amount of light produced by the bioluminescence reaction. Varying dilutions of S-Gluc solutions 0.07, 0.21, 0.36 and 0.5× was used in each well to form different immobilized densities respectively. Calibration standards for different amount of immobilized enzyme molecules obtained by incubating varying enzyme concentrations. FIGS. 3C and 3D illustrate surface and intensity plot of integrated signal for the immobilized enzyme concentrations obtained by perfusing CTZ inside the microchannel. FIG. 3E illustrates a calibration curve for signal obtained from varying immobilized enzyme concentrations. Error bars represent the standard deviation from the average light intensity produced (RLU μm-2s-1) calculated from area under the curve for 10, 20 and 30 second integrated times respectively.

FIGS. 4A & 4B represent the bioluminescence and fluorescence images of luciferase and fluorophore conjugated EGF-EGFR complex on live A431 cells. FIG. 4C shows bioluminescent signal emission profiles from square and patterned cell islands upon perfusion of coelenterazine into the microchannel at different time intervals. FIG. 4D shows an integrated bioluminescence signal plot from two representative square cell islands containing 315 cells and 298 cells respectively.

FIG. 5A illustrates confocal slice of H9c2 cells showing surface expression of β1 adrenergic receptors labelled with pAb conjugated s-AF 488 (green). Nuclei have been stained with DRAQ5 (red). FIG. 5B shows bioluminescent signal emission profiles from square cell islands containing H9c2 cells with a $C_n$ of 75 and 63 respectively. The emission profile of A431 cells is also shown in this plot to compare the signal intensities between the two cell lines grown with the same cell seeding area, $C_{sa}$.

FIG. 6A illustrates scanning electron photomicrograph of a 6 μm thick PDMS layer coated on top of a glass coverslip. This thin coating of PDMS was essential to restrict cell attachment in areas which were not treated with fibronectin. FIG. 6B shows a phase contrast image of A431 cell island cultured inside the microfluidic channel. FIG. 6C shows a fluorescent b/w (stitched) image of Fibronectin-Alexa 546 pattern on glass coverslip.

FIGS. 7A-7C illustrate the characterization of A431 and H9c2 cells. FIG. 7A is a confocal 3D reconstruction of a single A431 cell in which the EGFR's are bound to EGF- TMR. The zoomed in Image is captured with a 60× (1.35NA) objective in a FV1000 Olympus confocal microscope. FIG. 7B shows a confocal image of fixed H9c2 cells (cardiomyocytes) expressing Beta Adrenergic receptor clusters. Receptors are labelled with NBD-Propranolol (non-selectively stains intra and extracellular β1, β2 and β3 receptors) while the nucleus is stained blue with DAPI. F-actin is observed using Phalloidin-Alexa Fluor 546 confirming the presence of actin filaments in smooth muscle cells. FIG. 7C shows fixed H9c2 cells (cardiomyocytes) expressing Beta Adrenergic receptor clusters. Receptors are labelled with NBD-Propranolol.

FIGS. 9A-9C show western blot detection of cell lysates subjected to Native PAGE. FIG. 9A shows $\beta_1$ AR-b*-pAB and $\beta_1$ AR-b*-pAB-s-GLuc complexes detected by chemiluminescence ((HRP)-conjugated anti-rabbit IgG antibody). (b&c) Intensity plots representing signals obtained from blots respectively. Using non-linear least square fitting (26), the data in FIG. 9B is fitted to three Gaussian curves (dotted line curves) with their mean sizes ($x_1$, $x_2$, $x_3$) corresponding to (831 kDa, 1115 kDa, and 1290 kDa) with variances ($\sigma_1$, $\sigma_2$, $\sigma_3$) corresponding to (216 kDa, 94 kDa, and 150 kDa) respectively. The data in FIG. 9C is fit to the distribution curve in FIG. 9B (dotted line curves) and a similar distribution with a 164 kDa shift with an intensity ratio of 3:1 was observed, revealing two s-Gluc molecules attached per b*-pAb.

MATERIALS AND METHODS

Microfluidic Device Fabrication

Figure 6D:
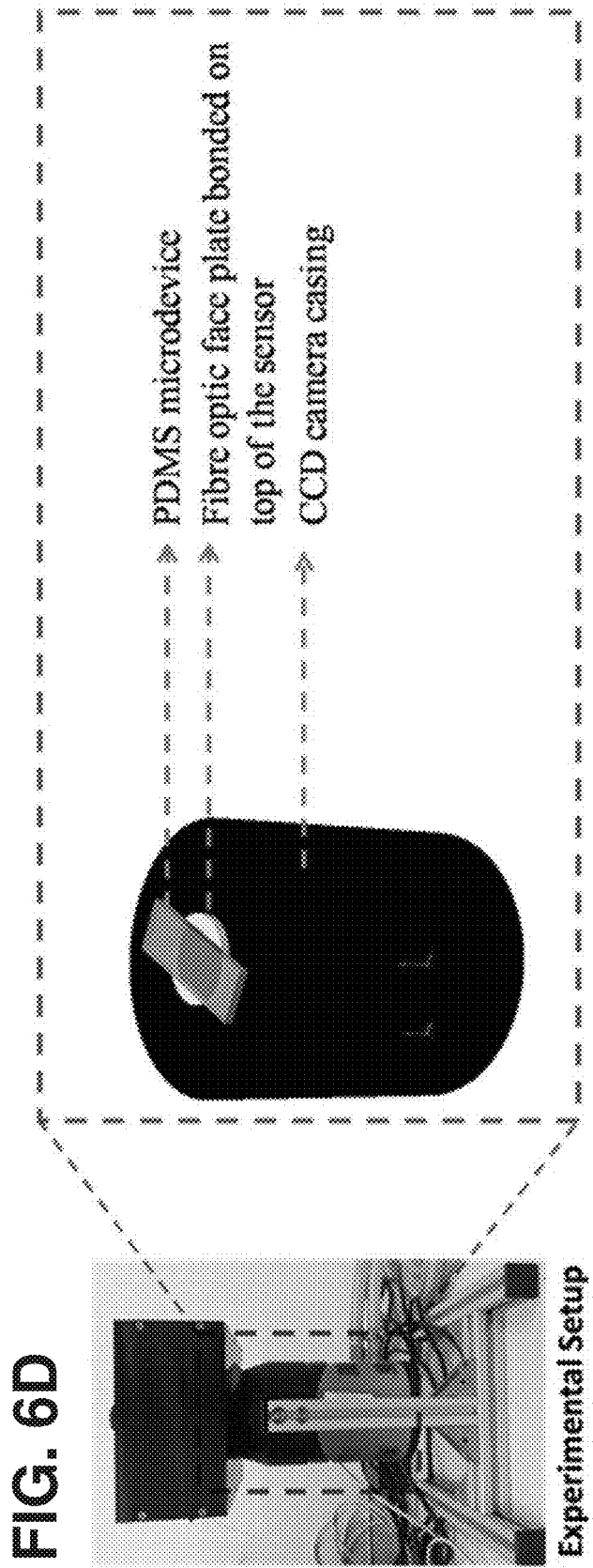
FIG. 6D shows an experimental setup of the CCD camera covered with a black light tight box. The PDMS microfluidic device is placed on top of the fibre optic face plate inside the black box.

The microdevice was fabricated using polydimethylsiloxane, PDMS (Sylgard 184, Dow Corning, USA) following conventional rapid prototyping and soft lithography techniques. A plastic photomask containing an array of channel profiles having the dimension 65 mm (L)×2 mm (W) was printed using a commercial photo plotting direct write laser imager. Standard photolithographic techniques were used to produce a silicon master with positive relief features using a negative photoresist (SU-8 2035, MicroChem Co, USA) to obtain features with 0.08 mm (H).

The silicon master was silanized with Trichloro (1H,1H, 2H,2H-perfluorooctyl)silane (Sigma Aldrich, Singapore) in a desiccator for 15 minutes at room temperature prior to the soft lithography steps in order to prevent undesired bonding of PDMS to the master. A mixture of PDMS-prepolymer and curing agent in 10:1 ratio, was poured over the master, degassed and cured for 4 hours at 65° C. The cured PDMS molds were peeled away from the master and cut to the size of standard glass slides (25 mm×75 mm). Channel inlets and outlets were punched using 1.5 mm diam. Harris Uni-Core™ puncher (Ted Pella Inc, USA). An additional hole was punched a few millimeters away from the main inlet using a 0.5 mm diam. Harris Uni-Core™ puncher, to facilitate the perfusion of the b*-Ab, s-GLuc and CTZ solutions respectively. The PDMS mold was then cleaned and rinsed with Isopropyl alcohol, de-ionized water and blow dried to remove traces of solvents. This was kept aside to bond with fibronectin patterned PDMS-glass coverslips.

Fibronectin Patterning on PDMS-Coverslips

A 25 mm×75 mm, glass coverslip (Electron Microscopy Sciences, USA) was coated with PDMS. Briefly, a PDMS mix consisting of 10:1 ratio of base to curing agent was mixed with hexane in a 1:1 ratio. Around 1.5 ml of the PDMS mix: hexane mixture was poured uniformly over the glass coverslip and spin coated at 6000 rpm for 30 seconds. The PDMS coated glass coverslips were baked in 60° C. for 4 hours resulting in ≈6 μm thick PDMS coating on the glass coverslip (FIG. 6A). The freshly baked PDMS-glass coverslips were then prepared to be coated with fibronectin patterns to facilitate cell adhesion.

The process of patterning fibronectin onto the PDMS coated glass slides is illustrated in FIG. 2A. Stencils of representative designs were made using a laser cutter (Universal Laser Systems, USA) which cut an array of squares (side—500 μm) onto 0.015 in thick silicone sheets (Stockwell Elastomerics, USA). The silicone stencils were then washed thoroughly with 70% ethanol to remove debris from the cutting process. The silicone stencil was then placed on top of the glass coverslip covering most of it except the areas which had the squares. The coverslip with the silicone stencil was then subjected to oxygen plasma for 30 seconds at 200 W radio frequency generator power and 450 mTorr oxygen pressure (March Instrument Incorporated, USA). Following the plasma treatment, 1 μL of 50 μg/mL fibronectin solution (Sigma Aldrich, Singapore) was placed on the exposed area and incubated at room temperature for 30 minutes. The exposed area was then washed thrice with DI water following which the stencils were removed. The patterned area was then covered with a small rectangular piece of silicone sheet and then exposed to plasma along with the PDMS-mold. The small rectangular silicone sheet was removed and the fibronectin patterned PDMS-coverslip was aligned and bonded to the PDMS molds in order to form microfluidic device. The microdevice was then incubated at 37° C. for 6 hours in order to facilitate tight bonding.

Cell Culture

A431 and H9c2 cells expressing epidermal growth factor receptors (EGFR's) and β-adrenergic receptors respectively were purchased from American Type Culture Collection (Manassas, USA). These cells were examined for their respective surface receptor expression using standard fluorescent ligands/antibodies with an additional actin stain for cardiomyocytes (FIG. 7B). The cells were cultured in DMEM supplemented with 4.5 g/L glucose, 4 mM L-glutamine, phenol red (Hyclone, USA), 1 mM Sodium Pyruvate, 10% FBS (Hyclone, USA), 50000 IU/L penicillin and 50 mg/L streptomycin. Cells were grown in standard T-75, tissue culture flasks kept inside a humidified incubator maintained at 37° C. and 5% CO2. The media used for the bioluminescence experiments conducted on the microchannel platform contained 1% Bovine Serum Albumin (Sigma Aldrich, Singapore), along with the aforementioned supplements except phenol red.

Figure 8A:
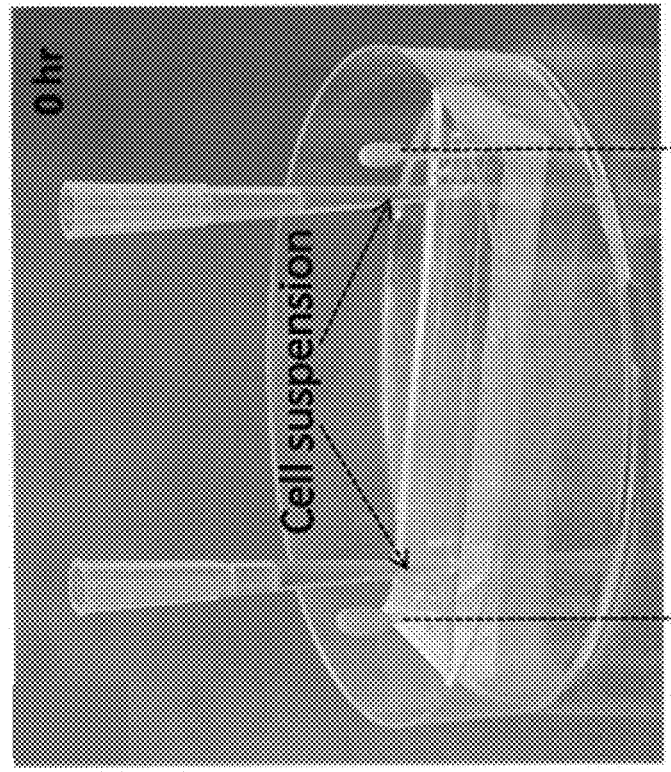
FIG. 8A illustrates cell seeding inside microchannel. Main inlet and outlet are closed while the cells are seeded through cell seeding inlet and collected through the seeding outlet.
Figure 8B:
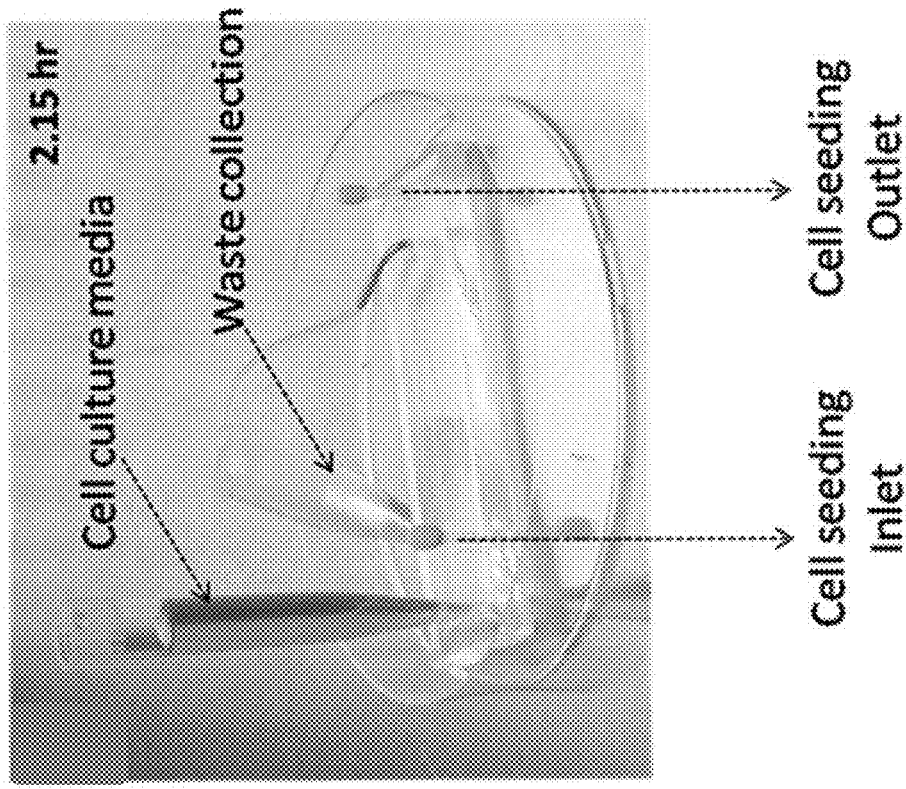
FIG. 8B shows perfusion of media inside the microchannel during cell growth. A 1 mL pipette tip continuously supplies media to cells over 7 hours or refilled until the cells are fully confluent in the patterned area.

Once the cells were 95% confluent for A431 cells and 70% confluent for H9c2 cells, they were trypsinized with 2× 0.5% Trypsin-EDTA (Caisson Labs, USA), centrifuged and re-suspended in DMEM complete medium at concentrations of 3 and 1 million cells/mL for A431 and H9c2 respectively. Prior to cell seeding inside the channel, the device was passivated with 1% Pluronics F-127 (Sigma Aldrich, Singapore) for 30 minutes. The channels were then flushed with cell culture media preceding cell seeding. 50 μL of cell suspension at the aforementioned concentrations were perfused inside different channels through the cell seeding inlets and outlets with micropipettes placed at both the ends acting as a source and a sink, while the other ports were blocked with stoppers. The micro-device was then incubated at 37° C. inside a 5% CO2 humidified incubator and was left undisturbed for a period of 2 hours to allow the cells to attach to the fibronectin patterns. The unbound cells were flushed away by perfusing media through the main inlet (FIG. 8B). The cell seeding inlets were blocked allowing a constant perfusion of cell culture media through the main inlet and outlet for 6-7 hours until the cells were confluent in the fibronectin patterned area (FIG. 2A). After the pattern area was confluent to form cell islands (see FIG. 6B), they were imaged using a normal bright field microscope, to estimate the total number of cells per island. The microfluidic device containing the cells were placed on top of the fibre optic face plate and made unmovable using a scotch tape. The main inlet was connected to a syringe pump (Kd Scientific, USA) controlling the flow of cell culture media while the receptor specific ligand, s-Gluc and CTZ were operated by individual syringe pumps and injected through the adjacent inlet. Ligand solutions used in the experiments were 100 nM biotinylated-EGF [b*-EGF] (Life Technologies, Singapore) for A431 cells, while a 1:100 dilution of 0.1 μg/μL β1 Adrenergic receptor pAb (Enzo Life Sciences, Switzerland) corresponding to the n-terminal region was used for the case of H9c2 cells. Initially, the receptors were allowed to saturate with the target ligand following which 100 nM streptavidin conjugated Gaussia luciferase [s-Gluc] (Avidity, USA) and 100 μM Coelenterazine [CTZ] (Avidity, USA) solutions were perfused sequentially. Flow velocities of 0.031 cm/s for 3 minutes were used during the ligand, s-Gluc and CTZ injection steps. Prior to the addition of the s-Gluc and CTZ respectively, cell culture media was perfused at 0.042 cm/s flow velocity for 2 minutes to remove any unbound/free molecules added previously into the channel. No loss or detachment of cells was observed during the aforementioned perfusion steps.

Optical Detection

Bioluminescence signal was detected using a deep cooled back illuminated CCD camera, PIXIS_XF 2048F (Princeton Instruments, USA) with a large area sensor 27.6×27.6 mm2 having a 13.5×13.5 μm pixel size (FIG. 6D). A fibre optic faceplate with a 6 μm fibre size was permanently coupled to the sensor in order to serve as an optical waveguide increasing the efficiency of signal transmission from the fluidic device to the sensor. Upon finally perfusing the substrate/coelenterazine solution into the channel, the camera recorded the bioluminescence signal from the cell islands continuously at 0.5 frame per second. There was negligible signal generated as a result of non-specific binding of s-Gluc to the cell islands which was tested by perfusing s-Gluc and CTZ solutions respectively without the b*-EGF. The 16-bit images were processed using ImageJ software. The measured signal intensity was corrected for the background noise and displayed as relative light units in the intensity plots presented in the results and discussion section.

Calibration Curve

An enzyme calibration curve was obtained by incubating different dilutions of the s-Gluc on a standard 22 mm×22 mm biotinylated glass coverslip (Microsurface inc., USA). This biotinylated coverslip with approximately 1014 biotin/cm2 served as a platform to immobilize different dilutions of s-Gluc. Briefly, a silicone gasket containing rectangular microwells (4 mm×1 mm×0.5 mm) was placed on top of the biotinylated coverslip to serve as a stencil. Different s-Gluc dilutions 0.07, 0.21, 0.36, 0.43, 0.57, 0.71, 0.86 and 1× of 1 μL volume were added on to the micro wells respectively and were incubated for half an hour to attain equilibrium. After incubation, the coverslip was rinsed with DI water following which the silicone stencil was removed and replaced by a PDMS block containing 0.3 mm wide microchannels (FIG. 2B). This was placed on the faceplate and signal was collected at 0.5 frame per second (or 2 s exposure time/frame) upon perfusing 100 μM CTZ solution.

Example 1

We describe a fast and easy method of quantifying cell surface receptors using quantitative bioluminescence and microfluidics. Cells are allowed to grow in a confined area within the microfluidic device by patterning fibronectin on the PDMS coated glass slide (FIG. 2A). This helps in determining the total number of cells present in a given area from which light is detected. Our method works by using biotinylated antibody that binds to a specific receptor of interest. Upon saturation of receptor by the bound biotinylated ligand, a streptavidin gaussia luciferase (s-Gluc) complex is bound to them. Light is produced when coelenterazine reacts with the luciferase. The total amount of bioluminescent signal, $S_T(RLU \cdot \mu m^{-2} s^{-1})$ generated by a finite number of cells ($C_n$) present in a cell seeded area $C_{sa}$, is proportional to the total number of receptors, $R_T$.

The number of receptors per cell, $R_{cell}$ can then be determined by $$R_{cell} = R_T C_{sa}/(C_n \cdot B^*_{LR}) \quad (1)$$

where $B^*_{LR}$ is the biotin/pAb labelling ratio.

Bioluminescent signal from a cell standard with a known $R_{cell}$ is first used to calculate the number of immobilized enzyme molecules in the calibration curve, (see calibration curve results section and FIG. 2B). This can then be used to determine $R_{cell}$ from H9c2 or any other cells in a similar manner. Furthermore, the effect of substrate (CTZ) concentration and effect of exposure time on the signal generated have been studied and optimized for this system.

Example 2

Effect of Substrate Concentration

The concentration of the substrate i.e. [CTZ] plays an important role in the light emission kinetics of the bioluminescent reaction. $S_T$ is less when a lesser concentration of the substrate [CTZ] is used. This is because at lower [CTZ] concentrations not all the enzyme molecules react with the substrate to produce light per unit time. However, when one uses a higher substrate concentration, almost all the enzyme molecules react with equal number of substrate molecules per unit time. Hence it is essential to operate at a sufficient amount of substrate concentration in order to carry out a better measurement. FIG. 3A shows the effect of substrate concentration [CTZ] on different immobilized s-Gluc dilutions (0.36, 0.5 and 0.71×) that were immobilized on the biotinylated glass coverslip. It is clear that lower [CTZ] concentrations 10 μM and 30 μM produce lesser amount of signal per unit time and area when compared to the higher concentrations 50 μM and 70 μM respectively.

Although there would be continuous perfusion of substrate molecules in a microfluidic flow system (as in this case), the user still has to operate at a sufficiently high substrate concentration so that all the enzyme molecules are actively involved in light production leading to better quantitative results. Thus a sufficiently high concentration 100 μM of CTZ was used in all the experiments conducted with cells.

Example 3: Effect of Exposure Time

The exposure time is also an important parameter for quantitative measurements with bioluminescence. Increasing the exposure time would improve the detection of fainter signals by ruling out instrumental delays caused while capturing continuous frames with lesser exposure times. The flash kinetic profile of Gaussia luciferase (Gluc) requires the user to detect signal instantaneously since the peak height as well as $S^T$ is an important factor while quantifying enzyme concentrations. FIG. 3B describes the effect of different exposure times on $S^T$ from increasing amount of immobilized enzyme molecules. Higher immobilized enzyme densities leading to more signal would saturate the sensor at longer exposure times. Hence, an appropriate balance should be struck between the exposure time and immobilized enzyme concentration so that the sensor does not get saturated while maintaining a good sensitivity. An exposure time of two seconds was found to best suit the experiments with A431 cells (over expressing EGFR's) with the given cell seeded area $C_{sa}$, while an exposure time of ten seconds was used in the case of H9c2 cells since the signal obtained from them was faint due to lower $\beta_1$ adrenergic receptor expression. In addition, the $C_n$ occupied in the $C_{sa}$ was also less since these cells were bigger than the former.

Example 4: Calibration Curve

The stock concentration of the s-Gluc complex is difficult to determine from protein assays since the streptavidin moiety is also accounted during quantification. Moreover, in order to quantify the cell bound receptors from adherent cells, it is necessary to obtain a calibration curve from immobilized enzymes since this best represents the system under study and avoids any loss in signal caused due to scattering or dispersion which could take place in solution phase free enzyme form. An alternate approach of considering a cell standard, to calculate the actual number of immobilized molecules for the calibration curve is suggested.

The epidermoid carcinoma A431 cell line was found to overexpress EGFR's ($R_{cell}=1.8 \times 10^6 - 3 \times 10^6$) on the cell surface by using different methods [1-4]. This was considered to be an appropriate cell standard for our study since it stably over expressed EGFR on the cell surface, as reported in the literature by using quantitative methods such as radiolabelling and positron emission tomography (PET).

Total bioluminescent signal $S_T$ (RLU·µm$^{-2}$s$^{-1}$) obtained from the A431 cells per unit area and time is determined by performing a flow experiment as mentioned in the methods section. $C_n$ was counted visually by capturing an image using a bright field microscope. The $R_{cell}$ value from the literature was then used to determine the $R_T$ as mentioned in equation 1.

An area normalized value of the $R_{cell}$ i.e. molecules/µm$^2$ and its $S_T$ (RLU·µm$^{-2}$s$^{-1}$) was used to calculate the immobilized receptor density for the 1× enzyme dilution by correlating to its signal (RLU·µm$^{-2}$s$^{-1}$) obtained from the calibration experiments. The immobilized densities from the other dilutions are interpolated by the same way as mentioned above. The immobilized enzyme densities and their corresponding $S_T$ (RLU·µm$^{-2}$s$^{-1}$) have been mentioned in table 2.

The surface plot in FIG. 3C shows the peaks representing integrated signal intensities obtained by varying the immobilized enzyme densities while FIG. 3D shows the corresponding intensity plot seen in two dimension. The total amount of signal generated by each spot is normalized per unit area and time and plotted against the total amount of immobilized S-Gluc molecules per unit area to obtain the calibration graph. FIG. 3E shows the calibration curve fit to a single parameter exponential growth model with an equation, $y = e^{0.0016x}$.

Example 4: Receptor Quantification from Cell Islands

A431 Cell Standard:
The signal generated by the microfluidic cell islands are used to determine the total amount of receptor molecules per cell. Prior to the microfluidic cell island experiments, the binding of the b*-EGF and s-Gluc complex to cell surface EGFR's were first validated on a 8-well confocal chamber and imaged with a 60×1.45NA objective, −70° C. cooled EMCCD camera (Andor Technology) to capture bioluminescence signal from the bound EGF (ligand) molecules. Briefly, the cells were labeled with b*-EGF first followed by the addition of s-Gluc which bound to the b*-EGF molecules. Coelenterazine (CTZ) was then added to the wells and simultaneously imaged with the aforementioned ultra-sensitive EMCCD camera. FIG. 4A shows a clear representation of the bioluminescent signal obtained from the cell surface in relation to the fluorescent signal obtained from EGF-TMR labeled A431 cells [see FIG. 4B]. Both the images show clear cell surface expression of EGFR's further supporting the fact that the binding of the b*-EGF and s-Gluc is specific to the receptor of interest.

The cell standard cultured on fibronectin islands is then placed on the lensfree platform to quantify $S_T$. FIG. 4C exhibits the bioluminescent signal over time obtained by perfusing CTZ to the s-Gluc conjugated antibody bound to the cell islands where cells were grown on each of the square and alphabetic (NUS) patterns. It is clear from FIG. 4D that the difference in cell numbers for the island area gives rise to more signal (RLU) correlating with the $C_n$.

Example 4: H9c2 Cell Sample

The back illuminated CCD camera used in our experiments increased the quantum efficiency to >95% allowing one to detect faint signals from the cell islands expressing low receptor numbers. The $\beta_1$ adrenergic receptor expression on H9c2 cells was found to be a suitable platform to validate our method. Rabbit $\beta_1$ adrenergic receptor pAb was first biotinylated following standard biotinylation procedure using the ChromaLink Biotinylation kit. UV measurements in NanoDrop instrument revealed that around 6 biotin molecules per antibody were conjugated using this kit. This conjugation or labelling ratio of biotin molecules was taken into account while determining $R_{cell}$ value. Following the biotinylation procedure the specificity of the $\beta_1$ pAb was checked by allowing them to bind to H9c2 cells. The $\beta_1$ adrenergic receptor targeted pAb on these cells were then labelled with streptavidin conjugated Alexa Fluor-488 (s-AF 488). Confocal imaging of these live cells revealed surface binding of the pAb as shown by a slice represented in FIG. 5A.

$R_{cell}$ value for the case of H9c2 cells were determined by fitting the total amount of bioluminescent signal produced per unit area and time, $S_T$ for H9c2 cells into the calibration curve equation. The number of $\beta_1$ adrenergic receptors on the surface of these cells was finally determined by further dividing this value by the biotin labelling ratio, $B^*_{LR}$ (corresponding to one biotin pAb binding to six s-Gluc) as mentioned in table 1. Additional experiments trying to validate the number of s-Gluc complexes on the cell surface were performed in well plates. The cells in the wells were lysed (refer methods section) following which the proteins were subjected to Native PAGE and western blotting. Intensity analysis of the bands obtained from western blot, revealed distinct curves for the $\beta_1AR$-b*-pAb and the b*-pAb-s-Gluc complexes (FIG. 9A). Fitting the b*-pAb-s-Gluc complexes curve (FIG. 9C) to the control distribution curves (FIG. 9B) revealed a 164 kDa shift suggesting that the b*-pAb bound to the $\beta_1AR$ had two of its sites occupied by the s-Gluc molecule.

Although this method allows protein separation under non-denaturing conditions, the protein charge and conformation along with the molecular weight, play an important role during protein separation in a Native PAGE. Considering the inherent properties of protein separation in a Native PAGE, the observed molecular weight difference might be apparent and underestimated due to these reasons. In addition, stearic hindrance at the cell surface caused due to receptor localization and clustering might also contribute to inadequate occupancy of the biotin sites per b*-pAb. Hence, the estimated $B^*_{LR}$ from the Native PAGE suggests the lower limit of the s-Gluc bound per antibody.

The $R_{cell}$ for the case of A431 cells provided in the literature is around $1.8 \times 10^6$ receptors/cell for which a calibration curve with a mono exponential fit were plotted. Considering the two $B^*_{LR}$ values the corresponding $\beta_1$ adrenergic receptor numbers obtained from the best fit equation for H9c2 cells are $3.12 \times 10^5$ to $<9.36 \times 10^5$ as mentioned in table 1. Given the inherent variation of $B^*_{LR}$, the $\beta_1$ adrenergic receptor numbers determined for the case of H9c2 cells are still found to be in a good agreement with that mentioned in the literature.

TABLE 1

Values used in the bioluminescent assay for A431 and H9c2 cell line. $R_{cell}$ calculated using this assay for H9c2 cell line is also mentioned.

| Cell line | $C_n$ | $B^*_{LR}$ | $S_T$ | $R_{cell}$ | $R_{cell\ literature}$ | References |
|---|---|---|---|---|---|---|
| A431/EGFR | 315 | 1 | 137.5 | $1.80 \times 10^6$ | $\approx 1.8 \times 10^6$ | 23, 24 |
| H9c2/$\beta_1AR$ | 75 | 6 (chromalink estimation) | 7.02 | $3.12 \times 10^5$ | | |
| H9c2/$\beta_1AR$ | 75 | min. 2 (Native PAGE approximation) | 7.02 | $<9.36 \times 10^5$ | $\approx 3.00 \times 10^5$ | 25 |

TABLE 2

Immobilized enzyme densities calculated from the standard cell intensity by interpolation.

| $S_T$ (RLU $\mu m^{-2} s^{-1}$) | | | Calibration | |
|---|---|---|---|---|
| | | | Molecules/$\mu m^2$ when $R_{cell}$ = | Molecules/$\mu m^2$ when $R_{cell}$ = |
| Average | S.D | Dilution | $3 \times 10^6$ | $1.8 \times 10^6$ |
| 5.49E-02 | 1.13E-03 | 0.07 | 183.39 | 109.93 |
| 2.39E-01 | 9.43E-03 | 0.21 | 550.17 | 329.79 |
| 8.14E-01 | 3.20E-02 | 0.36 | 916.95 | 549.64 |
| 1.14E+01 | 3.52E-01 | 0.43 | 1100.34 | 659.57 |
| 1.48E+01 | 1.24E+00 | 0.57 | 1467.12 | 879.43 |
| 1.60E+01 | 1.16E+00 | 0.71 | 1833.89 | 1099.29 |
| 3.32E+01 | 4.24E+00 | 0.86 | 2200.67 | 1319.14 |
| 5.88E+01 | 1.23E+01 | 1 | 2567.45 | 1539.00 |
| Best fit equation | | | $y = e^{0.0016x}$ | $y = e^{0.0026x}$ |

REFERENCES

1. De Jong L A A, Uges D R A, Franke J P, & Bischoff R (2005) Receptor-ligand binding assays: Technologies and Applications. Journal of Chromatography B 829(1-2):1-25.
2. Ahmed A (2003) Myocardial beta-1 adrenoceptor down-regulation in aging and heart failure: implications for beta-blocker use in older adults with heart failure. European Journal of Heart Failure 5(6):709-715.
3. Guttman M (1992) Dopamine receptors in Parkinson's disease. Neurologic Clinics 10(2):377-386.
4. DeBlasi A, O'Reilly K, & Motulsky H J (1989) Calculating receptor number from binding experiments using same compound as radioligand and competitor. Trends in Pharmacological Sciences 10(6):227-229.
5. Ianoul A, et al. (2005) Imaging nanometer domains of [beta]-adrenergic receptor complexes on the surface of cardiac myocytes. Nat Chem Biol 1(4):196-202.
6. Abulrob A, et al. (Nanoscale imaging of epidermal growth factor receptor clustering. Journal of Biological Chemistry 285(5):3145.
7. Hausmann M, et al. (2006) Near-field scanning optical microscopy in cell biology and cytogenetics. METHODS IN MOLECULAR BIOLOGY—CLIFTON THEN TOTOWA— 319:275.
8. Edidin M (2001) Near-Field Scanning Optical Microscopy, a Siren Call to Biology. Traffic 2(11):797-803.
9. Maguire C A, et al. (2009) Gaussia Luciferase Variant for High-Throughput Functional Screening Applications. Analytical Chemistry 81(16):7102-7106.
10. Cui K, Xu X, Zhao H, & Wong S T C (2008) A quantitative study of factors affecting in vivo bioluminescence imaging. Luminescence 23(5):292-295.
11. Sadikot R T & Blackwell T S (2005) Bioluminescence Imaging. Proceedings of the American Thoracic Society 2(6):537-540.
12. Hodgson L (2008) New Approaches to In-Cell Detection of Protein Activity: Genetically Encoded Chemiluminescence Probes Pave the Way to Robust HTS Assays. ACS Chemical Biology 3(6):335-337.
13. Zhang Y, Phillips G J, Li Q, & Yeung E S (2008) Imaging localized astrocyte ATP release with firefly luciferase beads attached to the cell surface. Analytical Chemistry 80(23):9316-9325.
14. Cali J J, et al. (2008) Bioluminescent assays for ADMET.
15. Tannous B A, Kim D E, Fernandez J L, Weissleder R, & Breakefield X O (2005) Codon-optimized Gaussia luciferase cDNA for mammalian gene expression in culture and in vivo. Molecular Therapy 11(3):435-443.
16. Chopra A (2008) Gaussia princeps luciferase.

17. Shimomura O & Teranishi K (2000) Light-emitters involved in the luminescence of coelenterazine. Luminescence 15(1):51-58.
18. Inouye S & Sahara Y (2008) Identification of two catalytic domains in a luciferase secreted by the copepod Gaussia princeps. Biochemical and Biophysical Research Communications 365(1):96-101.
19. Inouye S & Shimomura O (1997) The Use of Renilla Luciferase, Oplophorus Luciferase, and Apoaequorin as Bioluminescent Reporter Protein in the Presence of Coelenterazine Analogues as Substrate. Biochemical and Biophysical Research Communications 233(2):349-353.
20. Barry R & Ivanov D (2004) Microfluidics in biotechnology. Journal of nanobiotechnology 2(1):2.
21. Weibel D B & Whitesides G M (2006) Applications of microfluidics in chemical biology. Current Opinion in Chemical Biology 10(6):584-591.
22. Fabricant R N, De Larco J E, & Todaro G J (1977) Nerve growth factor receptors on human melanoma cells in culture. Proceedings of the National Academy of Sciences 74(2):565-569.
23. Felder S, LaVin J, Ullrich A, & Schlessinger J (1992) Kinetics of binding, endocytosis, and recycling of EGF receptor mutants. The Journal of cell biology 117(1):203-212.
24. Velikyan I, et al. (2005) Preparation and Evaluation of 68Ga-DOTA-hEGF for Visualization of EGFR Expression in Malignant Tumors. Journal of Nuclear Medicine 46(11):1881-1888.
25. Ianoul A, et al. (2005) Imaging nanometer domains of $β^2$-adrenergic receptor complexes on the surface of cardiac myocytes. Nature chemical biology 1(4):196-202.
26. Markwardt C B (2009) Non-linear least squares fitting in IDL with MPFIT. arXiv preprint arXiv:0902.2850.

The invention claimed is:

1. An assay device for the dynamic analysis of cell surface and/or intracellular ligand/receptor expression by live cells, comprising:
   a cell culture support having one or more cell culture channels, wherein said channel[s] comprise a cell support matrix comprising one or more cell adhesion/cell growth factors over all or part of the cell culture channel[s] to provide a cell culture surface, wherein said cell culture channel[s] each comprise:
   i) first and second openings positioned at or near the ends of said cell culture channel[s] to provide fluid passage into said cell culture channel[s], wherein said first and second openings are adapted to receive cell growth medium,
   ii) a third opening, optionally closable, positioned separately from the first or second openings, and in fluid contact with said cell culture channel[s], wherein said third opening is adapted to receive a sample comprising one or more cell types, and
   iii) a fourth opening, optionally closable, positioned separately from said first, second and third openings and in fluid contact with said cell culture channel[s], wherein said fourth opening is adapted to receive a sample comprising a binding agent that specifically binds a cell surface and/or intracellular ligand/receptor.

2. The device according to claim 1, wherein said cell culture support comprises a plurality of cell culture channels.

3. The device according to claim 1, wherein said cell culture support comprises silicone.

4. The device according to claim 3, wherein the silicone is polydimethylsiloxane.

5. The device according to claim 1, wherein said cell culture support comprises plastic or polystyrene or nylon.

6. The device according to claim 1, wherein said cell support matrix comprises one or more cell adhesion proteins selected from the group consisting of fibronectin, laminins, collagens, and adherens.

7. The device according to claim 1, wherein the one or more cell culture channels comprises the same cell support matrix.

8. The device according to claim 1, wherein the one or more cell culture channels comprises a different cell support matrix.

9. The device according to claim 1, wherein said device comprises one or more cell types.

10. The device according to claim 9, wherein said one or more cell types comprise a mammalian cell.

11. The device according to claim 10, wherein said mammalian cell is a non-human primate cell, mouse cell, rat cell, hamster cell, or rabbit cell.

12. The device according to claim 10, wherein said mammalian cell is a human cell.

13. The device according to claim 10, wherein said mammalian cell is an epidermal keratinocyte, a fibroblast, an epithelial cell, a neuronal glial cell, a neural cell, a hepatocyte, a hepatocyte stellate cell, a mesenchymal cell, a muscle cell, a cardiomyocyte, a myotube cell, a kidney cell, a blood cell, a pancreatic β cell, or an endothelial cell.

14. The device according to claim 13, wherein said mammalian cell is a cardiomyocyte.

15. The device according to claim 10, wherein said mammalian cell is a cancer or tumour cell.

16. The device according to claim 9, wherein said one or more cell types comprise a stem cell.

17. The device according to claim 16, wherein said stem cell is an embryonic stem cell/embryonic germ cell which is a pluripotent cell and not a totipotent cell.

18. The device according to claim 16, wherein said stem cell is a cancer stem cell.

19. The device according to claim 1, wherein said device is a microfluidic device.

20. A cell culture apparatus comprising:
   the assay device according to claim 1 in fluid contact with a source of cell growth medium, wherein the cell growth medium flows through said device to provide cell growth nutrients to cells contained within said assay device.

21. A method to assay expression of one or more ligands/receptors expressed by a cell, comprising:
   i) adding to the assay device according to claim 1 via at least one of the openings, at least one binding agent that binds one or more ligands/receptors expressed by a cell contained within said cell culture channel, wherein said binding agent is detected, either directly or indirectly, by a detectable label; and
   ii) detecting the binding of the binding agent to said one or more ligands/receptors as a measure of the presence of said ligand/receptor.

22. The method according to claim 21, wherein said binding agent is a biomolecule.

23. The method according to claim 21, wherein said binding agent is an antibody or antibody binding fragment.

24. The method according to claim 21, wherein said binding agent is a ligand that specifically binds said receptor.

25. The method according to claim 21, wherein said binding agent is a receptor that specifically binds said ligand.

26. The method according to claim 21, wherein said detectable label is a bioluminescent label.

27. The method according to claim 26, wherein said binding agent is a fusion protein comprising a polypeptide binding agent fused in frame to a bioluminescent polypeptide.

28. The method according to claim 26, wherein said bioluminescent polypeptide is a luciferase or a modified luciferase.

29. The method according to claim 21, wherein said device comprises a plurality of cell culture channels comprising one or more cell types arranged in an array and adapted to be read by an array reader.

30. The method according to claim 21, wherein said method is a diagnostic or prognostic method and said cell sample is an isolated biological sample from a subject.

31. The method according to claim 30, wherein said subject is human.

32. A screening method identify agents that modulate the activity of a cell, comprising:

i) adding to the device of claim 9 via at least one of the openings, at least one test agent to be screened for biological activity; and ii) measuring the activity of the test agent compared to a device or channel that has not been exposed to said test agent.

33. The method according to claim 32, wherein said assay includes the steps of:

i) collating the activity data;

ii) converting the collated data into a data analysable form; and optionally iii) providing an output for the analysed data.

34. The method according to claim 32, wherein said agent is a small organic molecule/biomolecule, antibody, ligand, peptide, nucleic acid or peptide aptamer, double stranded RNA, or small inhibitory RNA.

* * * * *